US006825218B1

(12) United States Patent
Godard et al.

(10) Patent No.: US 6,825,218 B1
(45) Date of Patent: Nov. 30, 2004

(54) SPHERICAL AGGLOMERATES OF TELITHROMYCIN, THEIR PREPARATION PROCESS AND THEIR USE IN THE PREPARATION OF PHARMACEUTICAL FORMS

(75) Inventors: Jean-Yves Godard, Le Raincy (FR); Valerie Rognon-Ravaux, Coubron (FR)

(73) Assignee: Aventis Pharma S. A., Antony Cedex (FR)

( * ) Notice: Subject to any disclaimer, the term of this patent is extended or adjusted under 35 U.S.C. 154(b) by 0 days.

(21) Appl. No.: 10/049,874

(22) PCT Filed: Aug. 28, 2000

(86) PCT No.: PCT/FR00/02393

§ 371 (c)(1),
(2), (4) Date: Jul. 1, 2002

(87) PCT Pub. No.: WO01/14393

PCT Pub. Date: Mar. 1, 2001

(30) Foreign Application Priority Data

Aug. 26, 1999 (FR) .......................................... 99 10810

(51) Int. Cl.[7] ..................... A61K 31/424; C07D 498/04

(52) U.S. Cl. ..................................... 514/338; 546/271.7
(58) Field of Search .......................... 546/271.3, 271.7; 514/338

(56) References Cited

FOREIGN PATENT DOCUMENTS

| EP | 0130160 | 1/1985 |
|----|---------|--------|
| EP | 0680967 | 11/1995 |
| JP | 02227130 | 9/1990 |

OTHER PUBLICATIONS

Graul et al, "HMR–3647, An Antimicrobial Ketolide", Drugs Future (1998) vol. 26, No. 6, pp. 591–597, XP 000909275.
Guillaume et al., "Spherical Crystallization of Meprobamate", Il Farmaco, vol. 48, No. 4, 1993, pp. 473–485.

*Primary Examiner*—Richard L. Raymond
(74) *Attorney, Agent, or Firm*—Balaram Gupta

(57) ABSTRACT

The invention relates to spherical telithromycin clusters and to a method for the production thereof characterized in that a telithromycin crystal suspension is prepared, said crystals are coated with a telithromycin insoluble phase which gradually crystallizes. The spherical telithromycin clusters are used in the preparation of micro-capsules.

6 Claims, 1 Drawing Sheet

SPHERICAL AGGLOMERATES OF TELITHROMYCIN, THEIR PREPARATION PROCESS AND THEIR USE IN THE PREPARATION OF PHARMACEUTICAL FORMS

This application is a 371 of PCT/FR00/02393 filed Aug. 28, 2000.

A subject of the present invention is spherical agglomerates of telithromycin, their preparation process and their use in the preparation of pharmaceutical forms.

Telithromycin or 11,12-dideoxy-3-de((2,6-dideoxy-3-C-methyl-3-O-methyl-alpha-L-ribohexopyranosyl)oxy)-6-O-methyl-3-oxo-12,11-(oxycarbonyl((4-(4-(3-pyridinyl)-1H-imidazol-1-yl)butyl)imino))-erythromycin is a product endowed with antibiotic properties of structure:

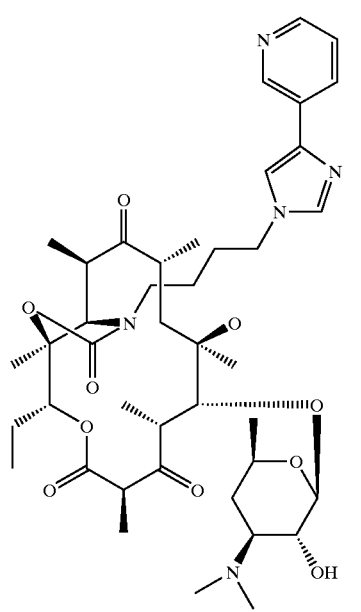

(I)

described and claimed in European Patent 680967.

The oral route is a preferred form of administration for this product. Some patients, children in particular, have difficulty in swallowing tablets and capsules and therefore it is desirable to have available other forms of administration such as for example oral suspensions, ready to use or prepared extemporaneously at the time of use.

Telithromycin is an active ingredient which has an unpleasant taste. Galenical forms must therefore be produced which mask the taste of the product yet preserve a good bioavailability.

The physico-chemical properties of telithromycin are such that they permit micro-encapsulation, i.e the coating of the active ingredient with a polymer or a mixture of polymers.

The micro-encapsulation can be carried out by spraying a polymer or by interfacial polymerization or by coacervation. In order to obtain a good micro-encapsulation, spherical particles of active ingredient must be available, particles which are neither too small, to prevent them from agglomerating among themselves, nor too large, in order that the dissolution is not too slow, and the particles must be spherical so that the covering of the active ingredient by the polymer is correct and in order to obtain good release kinetics for the active ingredient.

A subject of the invention is spherical agglomerates of telithromycin.

The spherical agglomerates are obtained as shown below by direct transformation of the crystals into masses of spherical shape.

As regards spherical agglomerates in general, reference may be had to the article by Frederica Guillaume and Anne-Marie Guyot-Hermann in Il Farmaco XLVIII 1993 pages 473 et seq.

The agglomerates of the invention permit a good micro-encapsulation and a subject of the invention is in particular the use characterized in that the spherical agglomerates are surrounded by a layer of polymer in order to obtain the sought galenical form, for example micro-capsules.

A subject of the invention is spherical agglomerates of telithromycin characterized in that the size of the particles is between 30 and 400 microns.

A quite particular subject of the invention is spherical agglomerates of telithromycin characterized in that the median size of the particles is situated between 80 and 150 microns and in particular spherical agglomerates of telithromycin characterized in that the median size of the particles is situated towards 100 microns, i.e. characterized in that half of the agglomerates are less than 100 microns in size.

A subject of the invention is also a process for the preparation of spherical agglomerates characterized in that a suspension of telithromycin crystals is prepared, and these crystals are then coated with a phase insoluble in telithromycin which progressively crystallizes.

A subject of the invention is in particular a preparation process characterized in that a solution of telithromycin in acetone is used.

A more particular subject of the invention is a preparation process characterized in that the crystallization takes place in an acetone/isopropyl ether mixture.

In a preferred embodiment, the crystallization is carried out between −5 and −15° C. The size of the spherical agglomerates is controlled by adjusting the stirring speed.

Finally a subject of the invention is spherical agglomerates of telithromycin as obtained by the preparation process described above.

The following example illustrates the invention without, however, limiting it.

EXAMPLE a) Preparation of the Acetone Solution

The following are introduced under nitrogen:

telithromycin 64 g anhydrous pure acetone 128 ml

Stirring is carried out under a slight nitrogen overpressure between 19° C. and 21° C. and a check is carried out to ensure that the dissolution is total.

If necessary, the quantity of water is added to obtain a 2.9% product, adding:

demineralized water 0.26 ml.

b) Crystallization

The following are introduced under nitrogen, into a double-casing reactor fitted with a mechanical stirrer, a thermometric probe and a nitrogen inlet:

isopropyl ether 640 ml anhydrous pure acetone 12.8 ml

The temperature is stabilized between 19° C. and 21° C. 5% by mass of the acetone solution is introduced, while stirring at 350 rpm.

Then, while still stirring at 350 rpm, the crystallization is initiated with 0.96 g of micronized telithromycin suspended by sonication in:

isopropyl ether 3.2 ml

Crystallization develops immediately after initiation.

Stirring is carried out for 15 minutes at 20±1° C. then the suspension is cooled down to −10±1° C. over 30 minutes.

The rest of the acetone solution is introduced:

acetone solution of telithromycin 157.2 g

Stirring is carried out for another 1 hour at −10° C.

c) Isolation

Thorough drying and washing by clarifications are carried out twice with, each time:

isopropyl ether 64 ml.

Drying is carried out in an oven at 40° C. under vacuum, followed by sieving on a 500 μm grid.

50.4 g of spherical agglomerates of telithromycin are obtained.

Granulometry

The size of the particles is determined by laser diffraction using a HELOS SYMPATEC® model granulometer.

The results obtained are the following: 10% of the particles have a diameter of <77 microns 50% of the particles have a diameter of <107 microns 90% of the particles have a diameter of <166 microns.

USE

Figure 1:
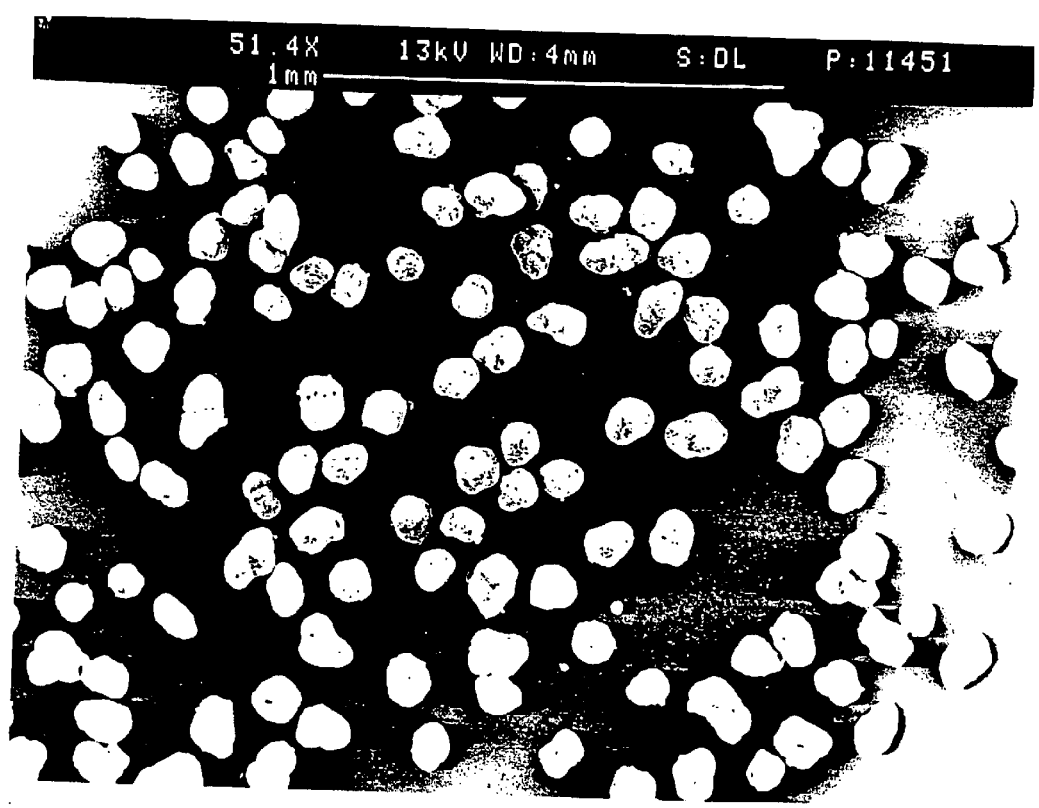
FIG. 1 represents agglomerates obtained by operating as shown above, the scale being 1 cm=150 microns.

The product of the example was used to prepare, by simple coacervation or by direct spraying of a suitable polymer, micro-capsules intended for the preparation of oral suspensions to be prepared extemporaneously.

The prepared suspensions are accepted by children and retain good release kinetics.

What is claimed is:

1. A process for the preparation of spherical agglomerates of telithromycin crystals, comprising preparing a suspension of telithromycin crystals, and coating the crystals with a phase in which telithromycin is insoluble from which telithromycin progressively crystallizes.

2. The process of claim 1, wherein a solution of telithromycin in acetone is used.

3. The process of claim 1, wherein the crystallization takes place in an acetone/ispropyl ether mixture.

4. The process of claim 1, where the crystallization is carried out between −5° C. and −15° C.

5. A method of treating a bacterial infection in a human comprising administering orally without an unpleasant taste to a human in need thereof an antibactercidally effective amount of a compound of a spherical agglomerate of telithromycin crystals surrounded by a layer of at least one polymer.

6. A method of forming a micro-encapsulated form of spherical agglomerates of telithromycin comprising surrounding spherical agglomerates of telithromycin with a layer of a polymer to obtain the micro-encapsulated form.

* * * * *